United States Patent
Truong

(10) Patent No.: US 11,235,167 B2
(45) Date of Patent: Feb. 1, 2022

(54) SYSTEMS AND METHODS FOR ADMINISTERING LIGHT THERAPY WHILE INCREASING PAIN THRESHOLD WITH DISTRACTION STIMULUS

(71) Applicant: L'Oreal, Paris (FR)

(72) Inventor: Lily Truong, Brooklyn, NY (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 16/863,529

(22) Filed: Apr. 30, 2020

(65) Prior Publication Data
US 2021/0339040 A1    Nov. 4, 2021

(51) Int. Cl.
*A61N 5/06*    (2006.01)

(52) U.S. Cl.
CPC .... *A61N 5/0616* (2013.01); *A61N 2005/0644* (2013.01); *A61N 2005/0651* (2013.01); *A61N 2005/0658* (2013.01); *A61N 2005/0664* (2013.01)

(58) Field of Classification Search
CPC .......... A61N 5/0616; A61N 2005/0651; A61N 2005/0644; A61N 2005/0658
See application file for complete search history.

(56) References Cited

U.S. PATENT DOCUMENTS

| | | |
|---|---|---|
| 2007/0027411 A1 | 2/2007 | Ella et al. |
| 2007/0149900 A1 | 6/2007 | Lin |
| 2007/0159592 A1 | 7/2007 | Rylander et al. |
| 2007/0255355 A1 | 11/2007 | Altshuler et al. |
| 2008/0091179 A1 | 4/2008 | Durkin et al. |
| 2008/0208104 A1 | 8/2008 | Bragagna et al. |
| 2014/0100489 A1 | 4/2014 | Altshuler et al. |
| 2014/0128780 A1 | 5/2014 | Kennedy et al. |
| 2014/0358132 A1 | 12/2014 | Eckhouse et al. |
| 2015/0088109 A1 | 3/2015 | Salomon |
| 2015/0290028 A1 | 10/2015 | Isserow et al. |
| 2017/0156664 A1* | 6/2017 | Belson ............... A61B 5/14539 |
| 2018/0236262 A1* | 8/2018 | Morries ............... A61K 31/135 |

FOREIGN PATENT DOCUMENTS

| | | | |
|---|---|---|---|
| EP | 2 140 911 A1 | 1/2010 | |
| FR | 3002148 A1 | 8/2014 | |
| KR | 101705067 B1 * | 2/2017 | ............. H01L 35/28 |
| WO | 2011/159317 A1 | 12/2011 | |

OTHER PUBLICATIONS

French Search Report and Written Opinion, dated Feb. 17, issued in French Application No. 2006539, filed Jun. 23, 2020, 11 pages.

* cited by examiner

*Primary Examiner* — Carl H Layno
*Assistant Examiner* — Aya Ziad Bakkar
(74) *Attorney, Agent, or Firm* — Christensen O'Connor Johnson Kindness PLLC

(57) ABSTRACT

A method of administering light treatment to a biological surface comprising administering light therapy from one or more light sources and administering distraction stimulus from one or more distraction mechanisms. The distraction stimulus is configured to distract a user from a discomfort caused by the light therapy.

21 Claims, 14 Drawing Sheets

SYSTEMS AND METHODS FOR ADMINISTERING LIGHT THERAPY WHILE INCREASING PAIN THRESHOLD WITH DISTRACTION STIMULUS

SUMMARY

Light therapies have been found to help treat a variety of afflictions. For example, skin blemishes develop for multiple reasons, some of which include harmful bacteria, blocked pores, irritation, imbalance in moisture or oil, etc. Typically, blemishes develop from an easily treatable early stage to a painful and difficult condition within a single day, often within hours of first sensing a new blemish. Without being bound to theory, it is believed that exposure to blue light may effectively treat blemishes. It is further believed that rapid treatment at the site of the blemish, immediately upon detection, prevents the growth of unsightly blemishes that may otherwise leave permanent scarring.

Additionally, with instances of skin cancer and other skin-related afflictions increasing, awareness about skin protection has been increasing. Skin protection can limit or prevent harm to skin from certain kinds of exposure such as exposure to ultraviolet (UV) electromagnetic radiation. Without being bound to theory, it is believed that exposure to near-infrared (NIR) light may have photoprotective qualities that prevent UV photodamage to the skin, prevent DNA damage, and minimize the effects of oxidative stress.

When blood flow to specific areas of the body is reduced, many people experience numbness, throbbing, muscle cramps, and other symptoms of low circulation. When these symptoms occur, they can be uncomfortable or even debilitating. It is believed that red light and infrared (IR) light treatment may improve blood circulation. Without being bound to theory, it is believed that exposure to red and IR light may also have anti-inflammatory qualities and may promote "anti-aging" effects, such as wrinkle reduction.

As the availability of visible light diminishes, people become more susceptible to seasonal depression and other mood effecting disorders. Without being bound to theory, exposure to broad spectrum light treatment is believed to enhance mood, as well as combat symptoms of seasonal depression.

While light therapies are thought to benefit a subject in a variety of ways, subject's ability to implement such treatment is limited by the depth of penetration of the light. The power density of the light treatment can be increased to further penetrate the skin. However, because of nerve surface fibers, penetrating greater than a certain depth results in discomfort and even pain. For example, blue light delivered at a power density greater than 100 mW/cm$^2$ may result in the subject experiencing pain. NIR light delivered at greater than 700 mW/cm$^2$ may result in the subject experiencing pain. For example, the pain threshold for red and IR light is believed to be at greater than 300 mW/cm$^2$. Without being bound to theory, it is believed that increasing the power density of the light treatment to improve skin penetration may benefit skin treatment.

Conventional portable cosmetic devices that provide light treatment have limited applicability and home-use capability. Since administering light treatment can be painful when light penetration exceeds a certain skin depth, as the power density increases, subject's ability to administer treatment to themselves is limited.

In some embodiments, a subject's pain threshold is increased by adding a distraction mechanism to the light therapy device. Examples of distraction mechanisms include temperature stimulus, such as warm air blown onto a biological surface, mechanical stimulus, such as brushes and actuators in contact with a biological surface, and electrical stimulus such as an electrical stimulus of above 2 mA applied to a biological surface. In some embodiments, distraction mechanisms act on the subject simultaneously with the light therapy. In some embodiments, a single distraction mechanism, such as temperature, may be applied with the light therapy. In other embodiments, a combination of distraction mechanisms (e.g. temperature and mechanical stimulus) may be applied with the light therapy. Without being bound to a theory, it is believed that any distraction mechanism could be coupled with any wavelength of light being administered and still effectively distract the subject from pain endured in treatment. In some embodiments of the present technology, light treatment is administered in conjunction with an auxiliary or distraction mechanism such as mechanical, electrical, and/or temperature stimulus. Such distraction allows a subject to continue light treatment past a power density that would otherwise be too painful to administer. Different embodiments of the present technology make home light treatments more accessible by allowing subjects to comfortably administer treatment to themselves.

In one embodiment, method of administering light treatment to a biological surface includes: administering light therapy from one or more light sources attached to a skincare device; and administering distraction stimulus from one or more distraction mechanisms attached to a device, where the distraction stimulus is configured to distract a user from a discomfort caused by the light therapy.

In an embodiment, the light source is configured to administer light at multiple wavelengths.

In another embodiment, the distraction mechanism is a mechanical distraction mechanism configured to provide mechanical stimulus to the biological surface.

In an embodiment, the mechanical stimulus includes stretching the biological surface.

In another embodiment, the mechanical stimulus includes brushing the biological surface.

In an embodiment, the distraction mechanism is a thermal distraction mechanism configured to provide thermal stimulus to the biological surface.

In another embodiment, the distraction mechanism is an electrical distraction mechanism configured to provide electrical stimulus to the biological surface.

In another embodiment, the method further includes contacting the device with the biological surface.

In another embodiment, the method further includes placing the device proximal to the biological surface.

In an embodiment, a skincare device includes: an end effector having: a light therapy unit including one or more light sources configured to administer a light therapy; and a distraction unit operably coupled to the light therapy unit. The distraction unit includes one or more distraction mechanisms configured to generate a distraction stimulus that distract a user from a discomfort caused by the light therapy.

In an embodiment, the one or more light sources are a first plurality of light sources configured to administer a light stimulus having a first wavelength. The distraction unit includes a second plurality of light sources configured to a administer a distraction stimulus at a second wavelength different from the first wavelength.

In another embodiment, the one or more light sources are a first plurality of light sources configured to administer a light stimulus at a first duty cycle. The distraction unit includes a second plurality of light sources configured to a administer a distraction stimulus at a second duty cycle different from the first duty cycle.

In an embodiment, the skincare device further includes a power source coupled to the light therapy unit and the distraction unit by a switch, the distraction unit being configured to administer the distraction stimulus by controlling the switch.

In an embodiment, the end effector is removably attached to a body.

In an embodiment, the one or more light sources include a first plurality of light sources configured to administer light within a given wavelength, and a second plurality of light sources configured to administer light therapy within a different given wavelength.

In an embodiment, the end effector includes an outer portion that at least partially surrounds an inner portion.

In another embodiment, the one or more distraction mechanisms include a mechanical distraction mechanism configured to provide mechanical stimulus to the biological surface.

In an embodiment, the one or more distraction mechanisms include a thermal distraction mechanism configured to provide thermal stimulus to the biological surface.

In another embodiment, the one or more distraction mechanisms include an electrical distraction mechanism configured to provide electrical stimulus to the biological surface.

In another embodiment, the one or more distraction mechanisms are located on the body of the device.

In another embodiment, the method further includes the one or more light sources are located on the body of the device.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

While the preferred embodiments of the invention have been illustrated and described, it will be appreciated that various changes can be made therein without departing from the spirit and scope of the inventive technology.

In one embodiment, the method includes administering light therapy coupled with a distraction stimulus. By providing distraction stimulus, a subject can administer light therapy having power density that exceeds his or her pain threshold. Therefore, light treatments with deeper penetration may be administered without causing as much discomfort to a subject. In some embodiments, the power density of the light treatment can be increased without increasing the intensity of the distraction stimulus, even as a subject's pain threshold is surpassed.

Figure 1:
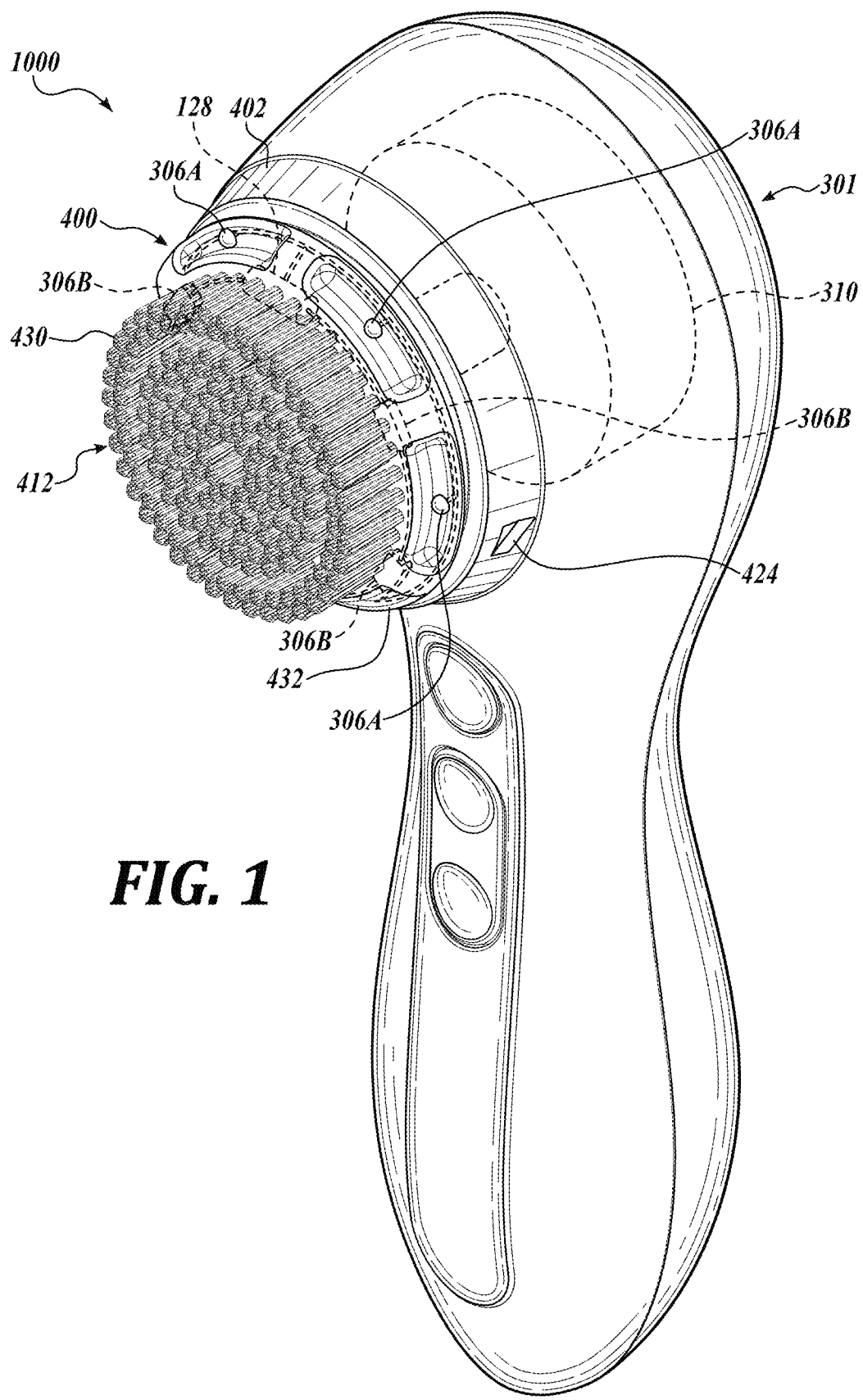
FIG. 1 is a schematic diagram of an example device in accordance with the present technology.
Figure 2:
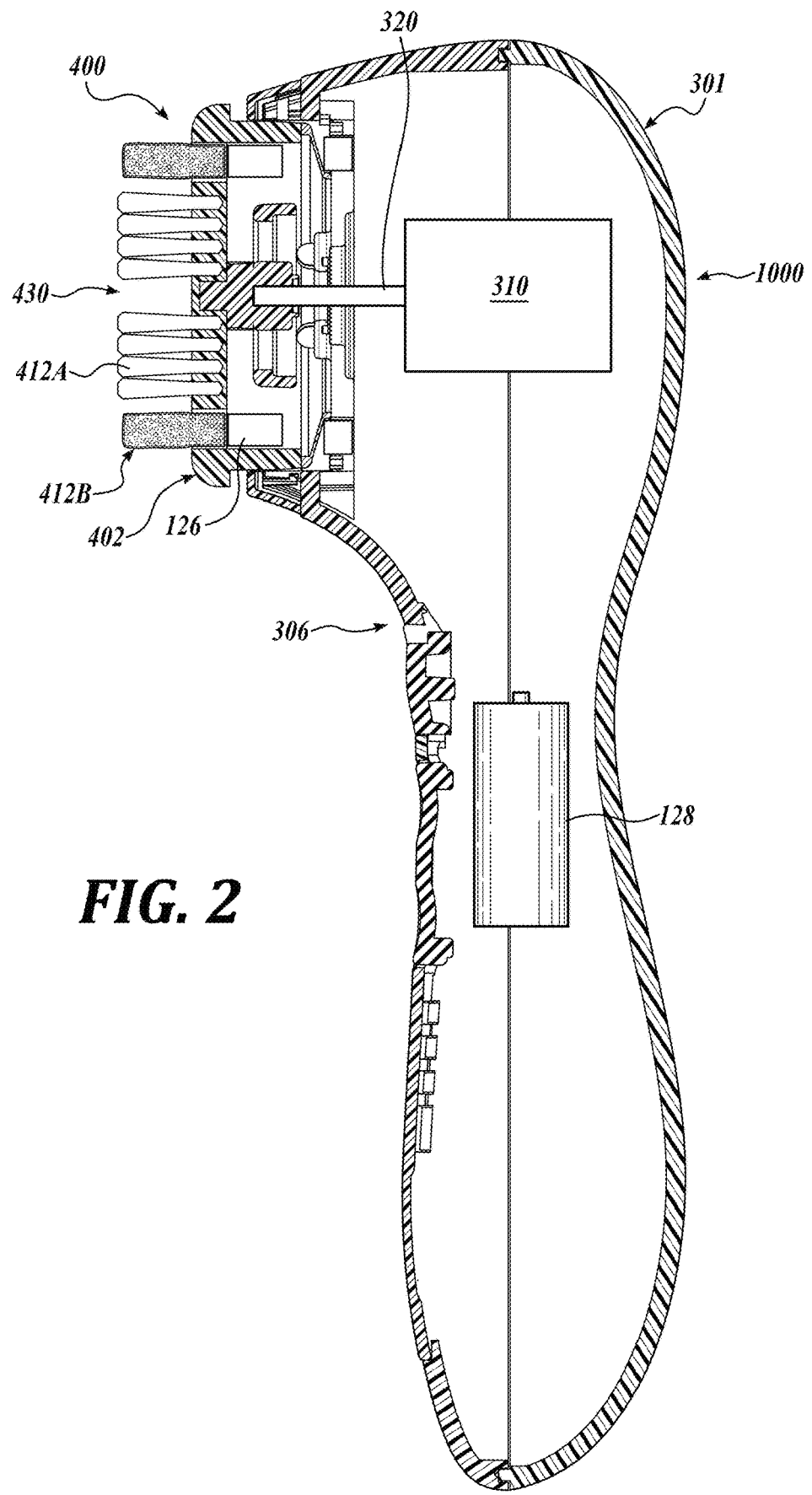
FIG. 2 is a schematic diagram of a cross section of an example device in accordance with the present technology.

FIG. 1 is an embodiment of a skincare device 1000 configured to provide light therapy. In some embodiments, the skincare device 1000 includes an end effector 400 (also referred to as a light therapy unit) that is removably attached to a body 301. In some embodiments, a base portion 402 of the end effector 400 is couplable to a motor 310 carried by the body 301. A battery 128 may be disposed in the base portion 402. In other embodiments, the battery 128 is disposed in the body 301 (as illustrated in FIG. 2). The battery 128 may power a distraction mechanism 412 and a plurality of light sources 306 that provide light therapy. In some embodiments, the light sources 306 all provide light therapy at a same peak emission wavelength (for brevity and conciseness referred to as "wavelength"). In other embodiments, a first plurality of light sources 306A provides light therapy at a given wavelength, and at least a second plurality of light sources 306B provide light therapy of a different wavelength. In some embodiments, there is only a single light source 306.

The battery 128 may power the motor 310. In some embodiments, other power sources are used, for example, capacitors. In some embodiments the movement or vibration of the motor 310 provides the distraction stimulus either in conjunction with the distraction mechanism 412, or on its own.

In some embodiments, the end effector 400 includes an inner portion 430 and an outer portion 432. One or more distraction mechanisms 412 may be attached to the inner portion 430, the outer portion 432, or both portions. In other embodiments, the distraction mechanism 412 is located on the body 301 of the device 1000. For simplicity, a brush head is illustrated as the distraction mechanism 412, but in other embodiments, other forms of distraction mechanisms 412 may be used. In some embodiments, the distraction mechanism 412 is a different form of mechanical element, such as an actuator. In other embodiments, the distraction mechanism 412 is a thermal element, such as illustrated in FIG. 2. In other embodiments, the distraction mechanism 412 produces electrical stimulus.

In some embodiments, the end effector 400 includes a switch 424 that operatively couples the distraction mechanism 412 and the light sources 306 with the battery 128. The battery 128 powers the distraction mechanism 412 and the light sources 306 when the switch 424 is actuated. The switch 424 may be a button configured to be actuated by a user, such as pressing the switch with a finger, but other configurations of the switch 424 are also possible. By actuating the switch 424, the light sources 306 are activated to emit light and the distraction mechanisms 412 are activated to provide distraction stimulus. In some embodiments, the switch 424 is located on the body 301 of the skin care device 1000.

In an embodiment, the battery 128 is a rechargeable battery configured to receive electrical power from an external source when, for example, electrical power of the rechargeable battery has been depleted. In another embodiment, the battery 128 is a single use battery. In an embodiment, a useable life of the single-use battery corresponds to an intended use interval of the end effector 400. As the end effector 400 is used over time, it may become worn, dirty, or otherwise unsuitable to provide its intended therapeutic benefits. In this regard, as the single-use battery 128 is used up and runs out of power, the end effector 400 may be configured to signal to a user that the end effector is ready for replacement, cleaning, reconditioning, and the like.

In operation, a user can actuate the switch 424 to turn on the light sources 306 and the distraction mechanisms 412. The user can then administer the light treatment. In operation, the distraction mechanism 412 provides distraction stimulus by acting on the biological surface. The light sources 306 illuminate a given region of the biological surface with light. In some embodiments the light source 306 provides light therapy to the user by contacting the biological surface. In other embodiments, the light source 306 provides light therapy while in proximity of the biological surface. By applying the distraction mechanism, the subject may be able to increase his or her pain threshold, thus enabling light therapy treatment at a higher power density. As previously explained, it is believed that irradiation of the biological surface with light provides desirable therapeutic results including treatment of blemishes, improved circulation, mood enhancement, etc.

FIG. 2 is a cross section of an example skin care device 1000 in accordance with the present technology. In some embodiments, the end effector 400 includes a base portion 402 couplable to a motor 310 through a shaft 320 carried by a body 301 that is separable from the end effector 400. Furthermore, a battery 128 is disposed in the body 301 and configured to power a distraction mechanism 412 and/or a light source 306. In some embodiments, the light source 306 is located on the body 301 of the device 1000. In another embodiment, the light source 306 is located on the end effector 400. The end effector 400 is comprised of an inner portion 430 and an outer portion 432.

In the illustrated embodiment, the end effector 400 includes a distraction mechanism 412A in the inner portion 430, illustrated as brush bristles. In some embodiments, the end effector 400 includes different distraction mechanisms, such as a thermal component or a component capable of delivering electrical stimulus 412B. In different embodiments, the distraction mechanisms 412 may be collectively referred to as a distraction unit.

The end effector 400 includes a second distraction mechanism, illustrated as a thermal element 412B. In some embodiments, the thermal element distraction mechanism 412B is heated or cooled by one or more thermal sources or sinks 126. Some non-exclusive examples of such thermal sources/sinks 126 are electrical heaters and Peltier cooling elements. In other embodiments, the thermal element may be heated through infrared red heating from a source of infrared radiation 126. The thermal sources/sinks 126 may be powered by electrical current from one or more batteries 128 or from a line source of power. The thermal element may be preheated or precooled to a set temperature that is either below or above skin temperature, depending on a desired effect on the user. In some embodiments, the thermal element includes phase-change materials that undergo solid/liquid phase-change at a temperature that is below or above the skin temperature. Generally, the phase-change materials have relatively high thermal capacity, thus being capable of operating for relatively long periods of time without thermal recharging. The thermal element may be deformable, thus approximating the contour of the skin in use. In some embodiments, the thermal element can heat/cool skin of the user without making physical contact with the user. For example, the thermal element may emit infrared waves to heat skin of the user.

In some embodiments, distraction mechanism 412B may be a different mechanism such as a component capable of delivering electrical stimulus. In some embodiments, distraction mechanism 412A and distraction mechanism 412B provide the same distraction stimulus at two different locations on the device 1000. Some embodiments include a distraction mechanism 412 in the inner portion 430 only. Other embodiments include a distraction mechanism 412 in the outer portion 432 only. In other embodiments, the distraction mechanism 412 is located on the body 301 of the device 1000.

In some embodiments, the motor 310 in the body 301 is coupled to the end effector 400. The motor 310 may be configured to oscillate the end effector 400 about an axis and/or plane of the end effector 400.

In operation, a subject administers light therapy by turning on the light source 306. Simultaneously, the distraction mechanism 412 contacts the biological surface. The brush distraction mechanism 412A may provide mechanical stimulus as the user manually brushes the biological surface. In some embodiments, the brush distraction mechanism 412A is driven by mechanical stimulus by the motor 310, which oscillates the distraction stimulus 412A while contacted with a biological surface. The thermal distraction mechanism 412B heats/cools the biological surface. Both distraction mechanisms 412 allow the subject to increase the power density of the light treatment while experiencing less discomfort during treatment.

Figure 3A:
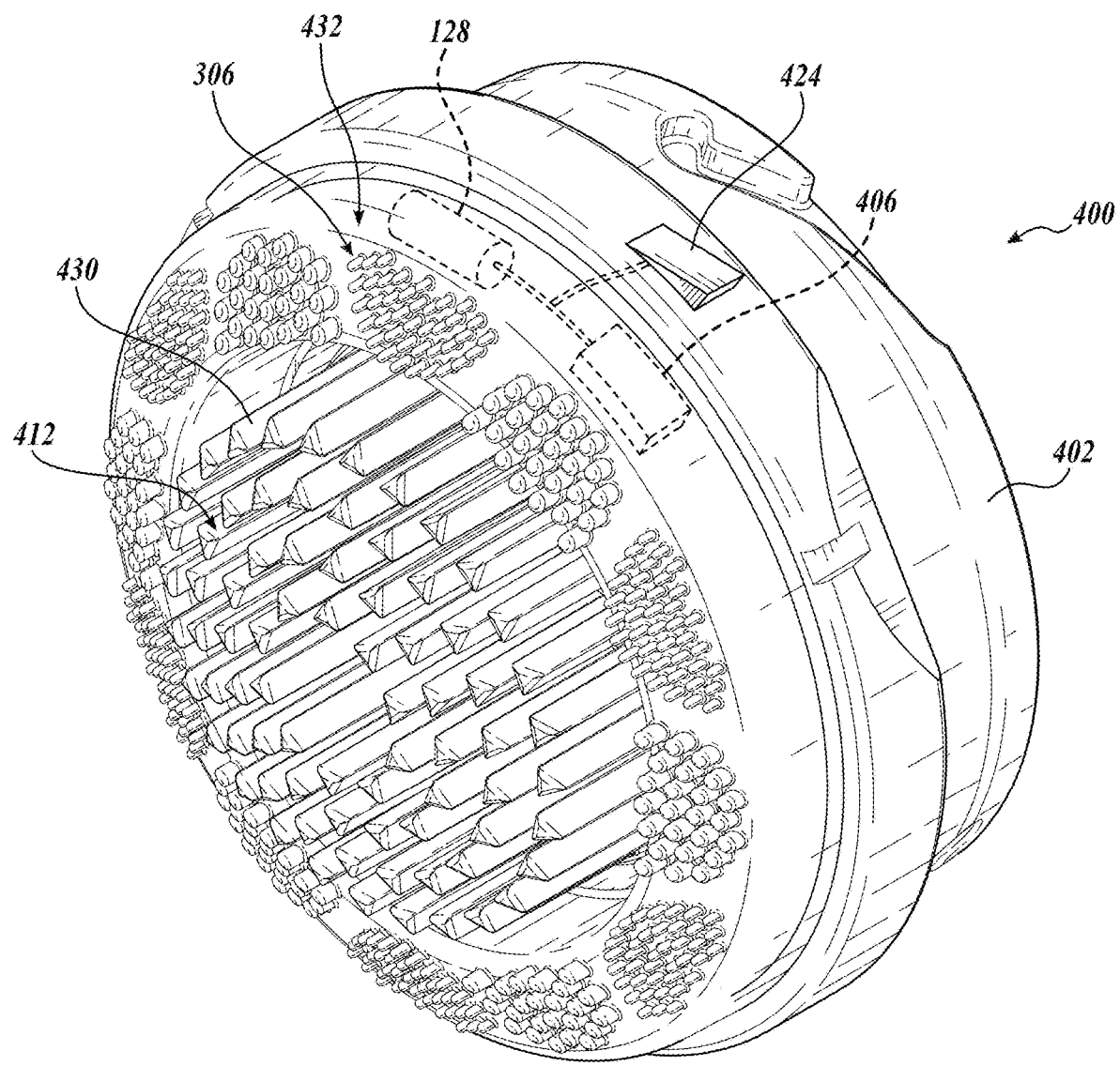
FIG. 3A is a schematic diagram of an isometric view of an example end effector of a device in accordance with the present technology.
Figure 3B:
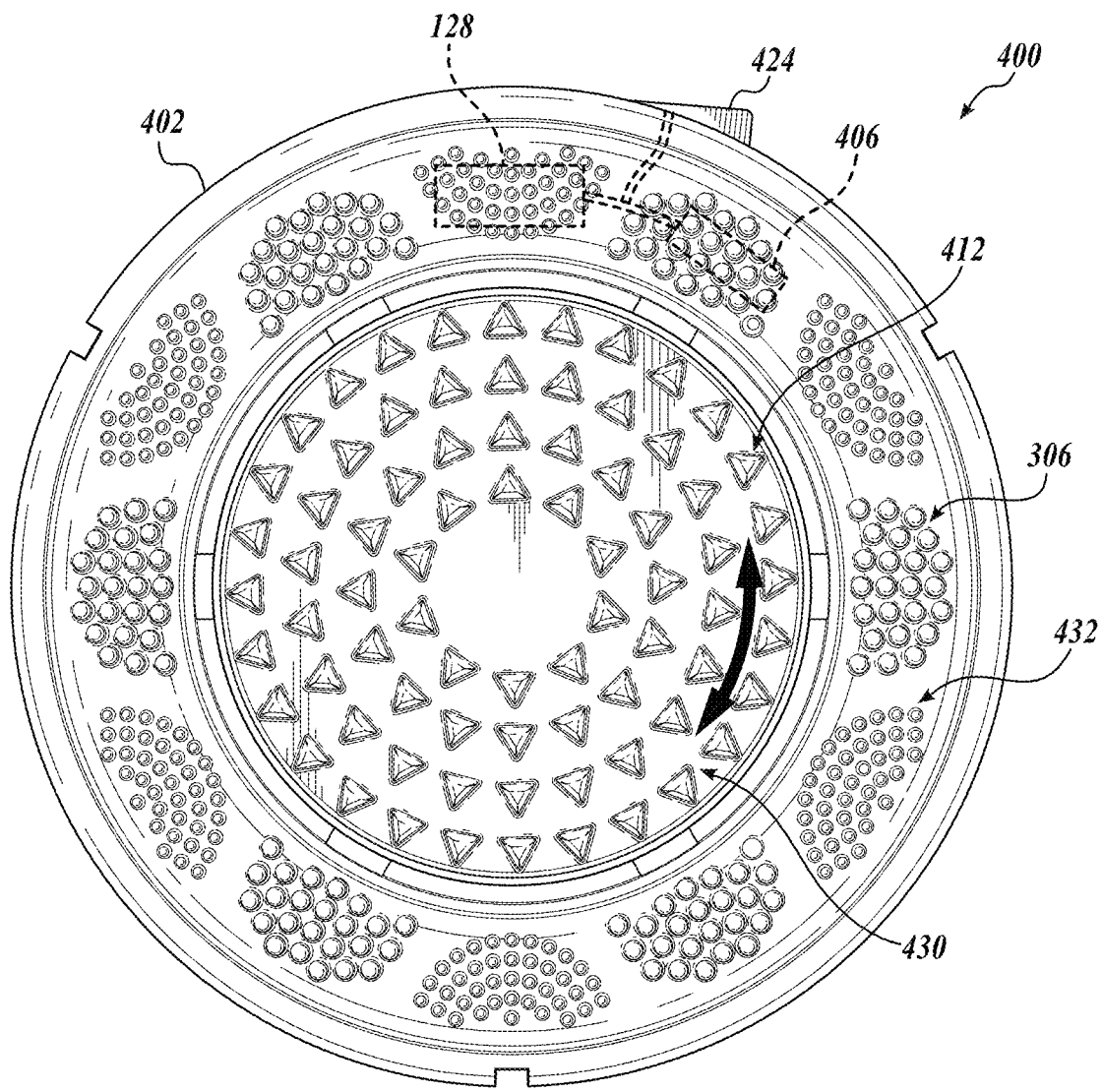
FIG. 3B is a schematic diagram of a plan view of an example end effector of a device in accordance with the present technology.

FIG. 3A-3B are views of an end effector 400 from two different angles. FIG. 3A is an isometric view of the end effector 400. FIG. 3B is a plan view of an end effector 400.

In the illustrated embodiment, the end effector 400 is shown separately from a body 301 for simplicity. The end effector 400 includes an inner portion 430 that is at least partially surrounded by an outer portion 432. In the illustrated embodiment, the inner portion 430 has a distraction mechanism 412. For simplicity, the distraction mechanism 412 is illustrated as a plurality of actuators, but the distraction mechanism 412 may also be a thermal, electrical, or mechanical component capable of delivering distraction stimulus.

The outer portion 432, includes a plurality of light sources 306. In some embodiments, the light sources 306 are configured to provide light therapy at a given wavelength. In some embodiments, the light sources 306 are configured to provide light therapy at a multitude of different wavelengths. In some embodiments, the light therapy device includes multiple light sources 306. The light source 306 may include one or more light emitting diodes, individually emitting light having a wavelength within a target range. In some embodiments, the light sources 306 may emit light at one wavelength, while the distraction mechanism 412 emits light at another wavelength different from the therapy wavelength. In some embodiments, the light sources 306 may emit light at one duty cycle, while the distraction mechanism 412 emits light at another duty cycle different from the therapy duty cycle. The light emitting diodes may be located on the inner portion 430 or the outer portion 432 of the end effector 400. In some embodiments, the light emitting diodes are located on the body 301 of the light therapy device (as illustrated in FIG. 2).

The end effector 400 has a battery 128 connected to a motion sensor 406. The battery and motion sensor 406 are connected to switch 424. In some embodiments, the switch 424 allows a subject to select a wavelength to be administered. By actuating the switch 424, the light sources 306 are activated to emit light and the distraction mechanisms 412 are activated to administer distraction stimulus.

As shown in FIG. 3B, the end effector 400 includes a motion sensor 406, such as an oscillation sensor, configured to generate a movement signal, such as an oscillation signal, indicative of movement of the end effector 400. In this regard, as end effector 400 is oscillated, as shown by the double headed arrow on the inner portion 430, the inner portion 430 moves. End effector 400 further includes a battery 128 coupled to the oscillation sensor 406. In an embodiment, a controller (not shown in FIG. 3B) includes logic that when executed by the controller causes the end effector 400 to perform operations. In an embodiment, such operations include actuating the end effector 400 based on a received oscillation signal. As the end effector 400 oscillates, a motion signal is received from a motion sensor 406, and the oscillation of the inner portion 430 or the outer portion 432 may be activated. Such activation of the inner portion 430 and/or the outer portion 432 in conjunction with motion of the end effector 400 is may provide mechanical distraction.

FIGS. 4A-4J are isometric views of example end effectors 400 of a device 1000. In the illustrated embodiments, the end effector 400 is a stand-alone device. In other embodiments, the end effector 400 is detachably couplable to a body 301. The end effector 400 includes an inner portion 430 and an outer portion 432.

Figure 4A:
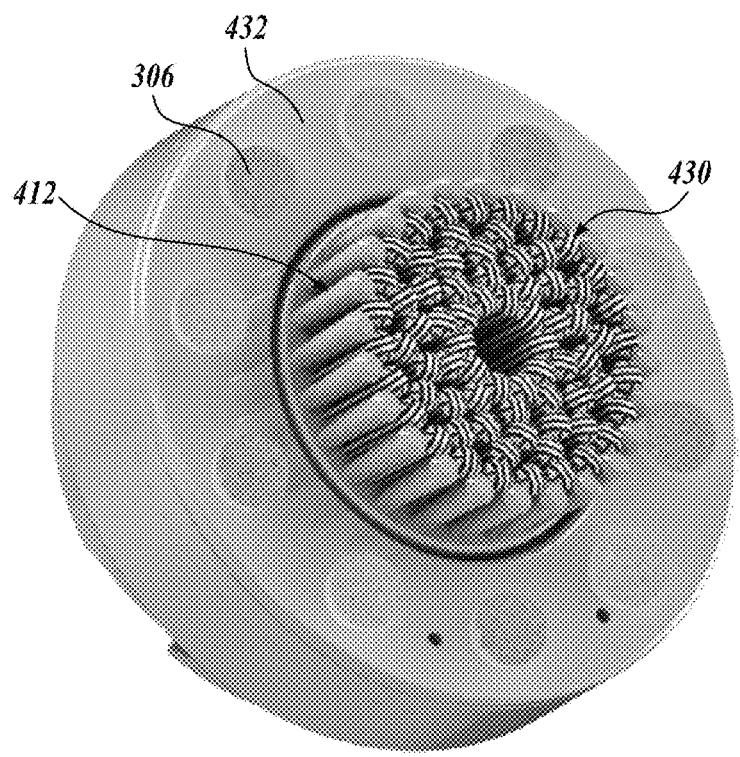
FIGS. 4A-J are isometric views of example end effectors of a device in accordance with the present technology.
Figure 4B:
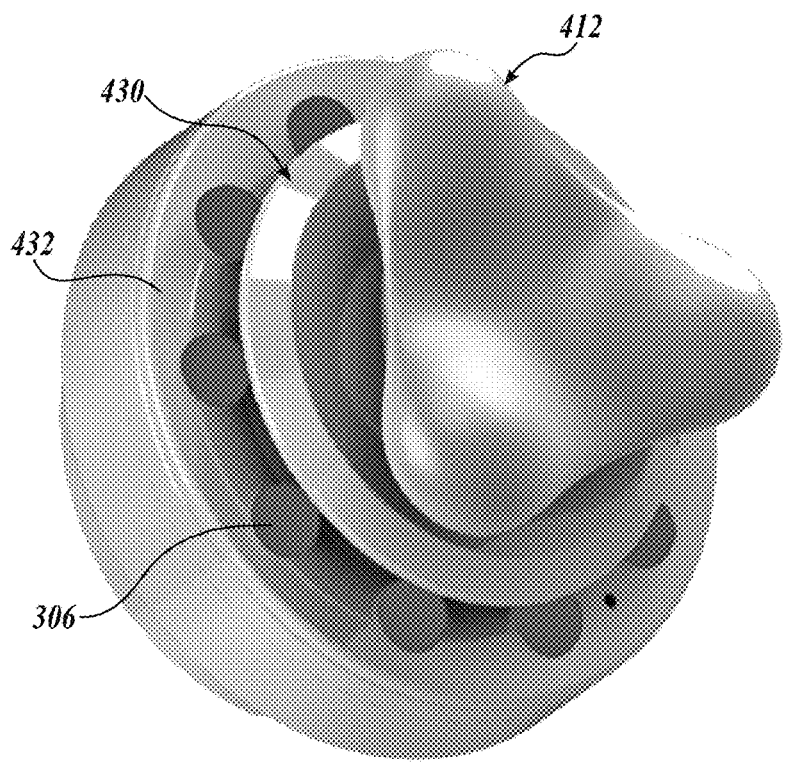

In some embodiments, the distraction mechanism 412 is mechanical. For example, FIG. 4A illustrates an end effector 400 with a distraction mechanism 412 in the form of brush bristles on the inner portion 430. A plurality of light sources 306 are shown on the outer portion 432. The brush bristle distraction mechanism 412 may be mechanically brushed across the biological surface to provide distraction. The distraction mechanism 412 may be operated by a motor 310 that is powered by a battery 128. In some embodiments, the inner portion 430 or outer portion 432 includes a motion sensor 406 (not illustrated in FIGS. 4A-4J) coupled to the distraction mechanism 412 to provide vibration or oscillation signal. The vibration source (e.g., motor 310) may vibrate the treatment device in multiple axes simultaneously. In other embodiments, the vibration source may vibrate the treatment device along only one axis. The vibration may be coupled to different distraction mechanisms 412. For example, in FIG. 4B, the vibration source (e.g., motor 310) is coupled with a distraction mechanism 412 in the form of a massager.

Figure 4C:
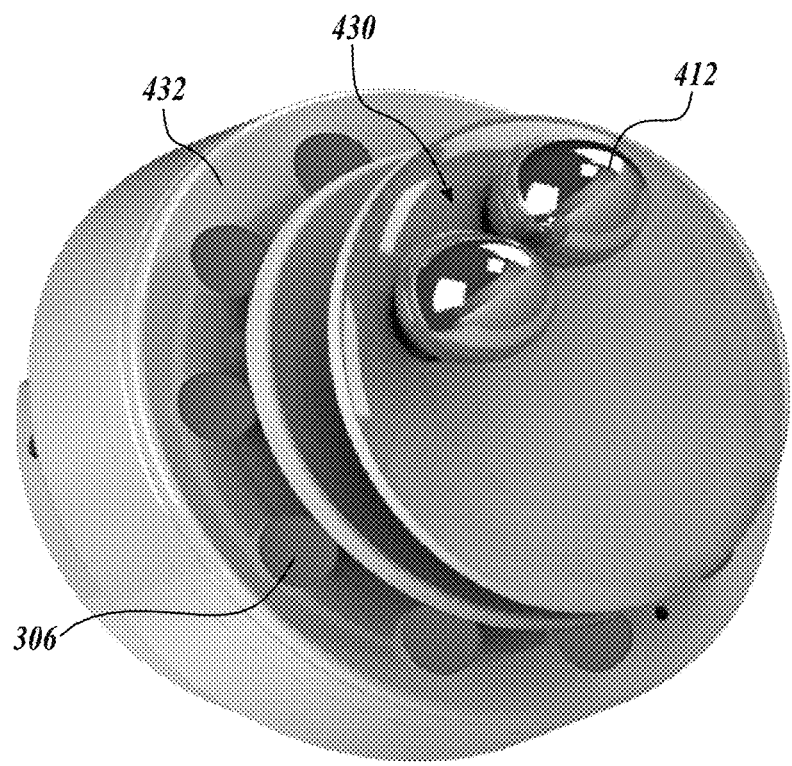

In some embodiments, the inner portion 430 or outer portion 432 of the light therapy device 1000 may have one or more actuating members acting as the distraction mechanism 412. For example, FIG. 4C illustrates an end effector 400 having a distraction mechanism 412 in the form of an actuator. Without being bound to theory, it is believed that the repeated tension and compression of the biological surface provides a distraction stimulus to the subject. In some embodiments, the actuating members move in opposite directions from each other, parallel to the biological surface. In some embodiments, the actuating members move towards each other, in turn compressing and releasing the biological surface. In some embodiments, the actuating members move away from each other, in turn stretching and compressing the biological surface. Light therapy by one or more light sources 306 is administered while the actuating members actuate the biological surface (e.g., skin of the user).

Figure 4D:
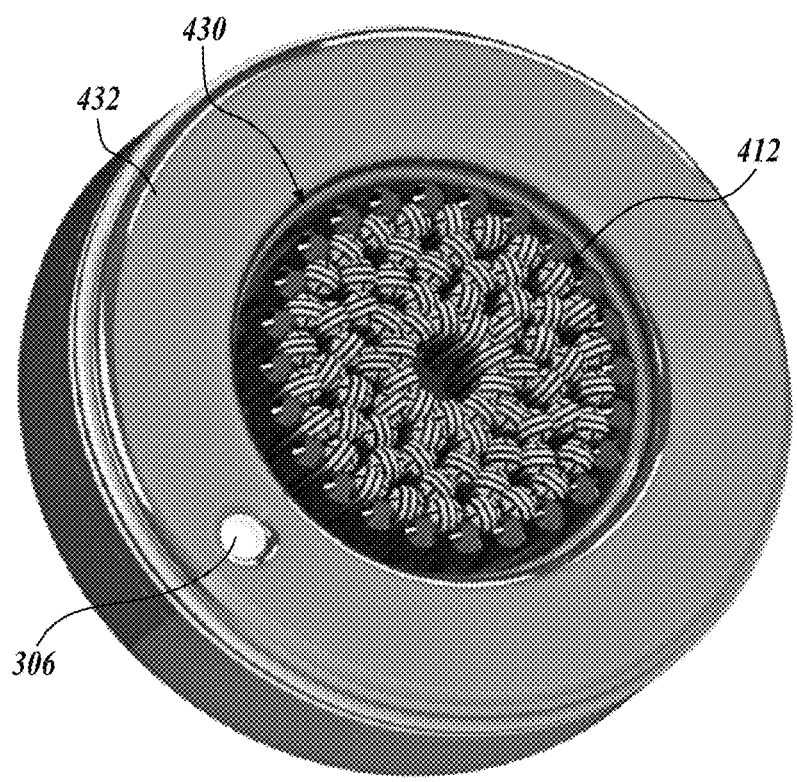
Figure 4E:
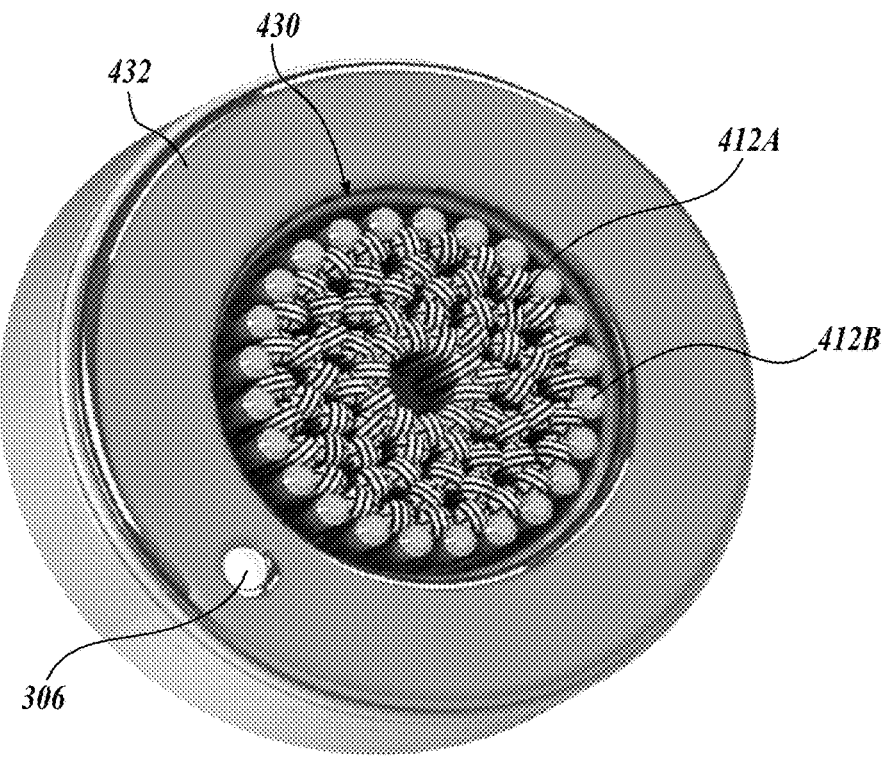

In some embodiments, the end effector 400 may include a single light source 306. For example, FIG. 4D is an end effector 400 with a single light source 306 located on the outer portion 432. Similarly, FIG. 4E is an end effector 400 that also has a single light source on the outer portion 432.

In some embodiments, the distraction mechanism 412 is a combination of different kinds of distraction stimuli. For example, as illustrated in FIG. 4E, the distraction mechanism 412A is brush bristles that are combined with a distraction mechanism 412B, a thermal element. In some embodiments, the distraction mechanism 412 and the light source 306 contact the subject's biological surface simultaneously to deliver treatment. The bristles of distraction mechanism 412A contact the biological surface of a subject in conjunction with the thermal element distraction mechanism 412B. The thermal element may be warmer or colder than skin of a user. In the illustrated embodiment, a centrally located brush distraction mechanism 412A is surrounded by the thermal element distraction mechanism 412B, but in different embodiments different arrangements of the thermal elements and bristles are also possible.

Figure 4F:
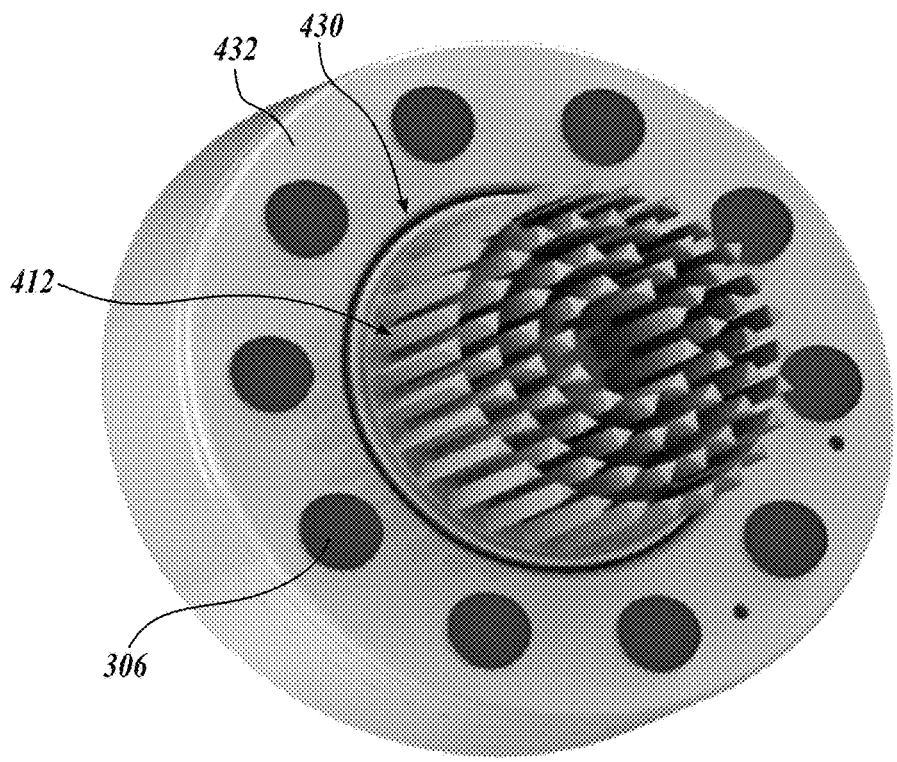
Figure 4G:
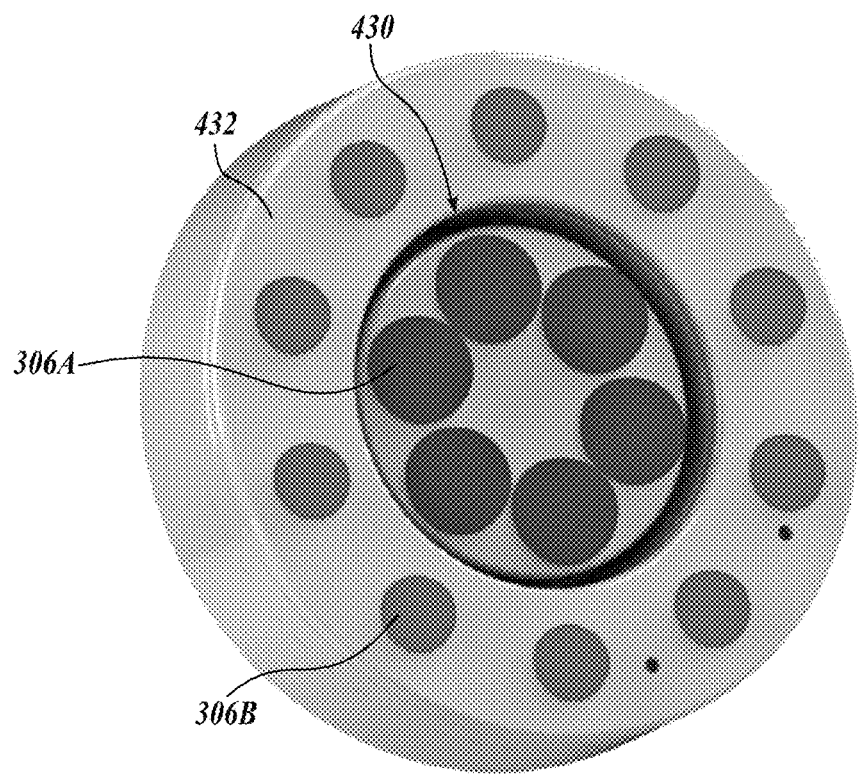
Figure 4H:
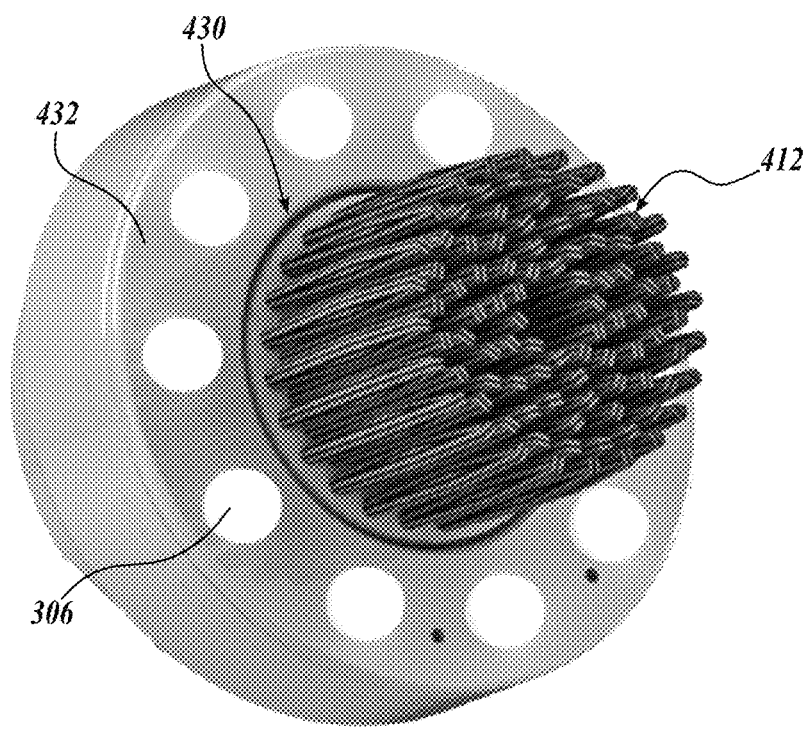

FIG. 4F is an example end effector 400 with an outer portion 432 and an inner portion 430. On the outer portion 432 is a light source 306, and on the inner portion 430 is a distraction mechanism 412. FIG. 4G is an example end effector 400 with light sources 306A and 306B located on both the inner portion 430 and the outer portion 432 and having no distraction mechanisms 412 on either portion. In some embodiments, the distraction mechanism 412 may be on the body of the device 301 instead of on the end effector 400.

In some embodiments, for example FIG. 4G, the light sources 306 can be applied directly to the biological surface. In other embodiments, for example FIG. 4H, the distraction mechanism 412 may be long enough to prevent the light sources 306 from directly contacting the biological surface, instead illuminating the region of biological surface from a distance.

Figure 4I:
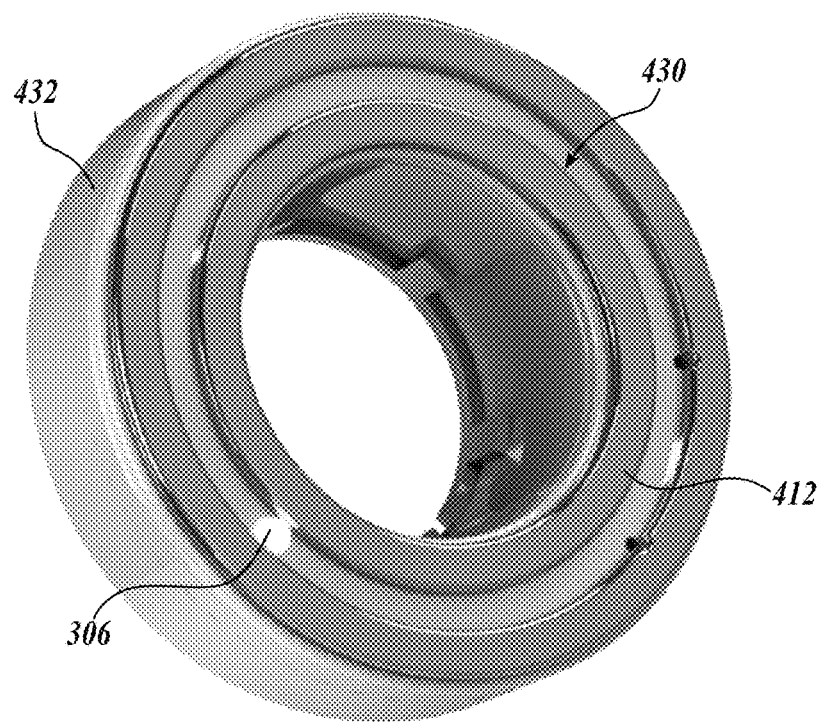

In some embodiments, as shown in FIG. 4I, the inner portion 430 has an opening in it. The opening may be centered or offset in any direction, and can be in different shapes such as circular, rectangular, polygonal, etc. Light treatment may be administered from a single light source 306 on the outer portion 432. The distraction may be provided by a distraction mechanism 412 that includes heating or cooling elements also located on the outer portion 432. In other embodiments, the end effector 400 has a distraction mechanism 412 configured to apply an electrical stimulus to a subject's biological surface. In some embodiments, the subject may deliver an electric stimulus at the point at which the muscle twitches, through distraction mechanism 412. The electrical component may be powered by a battery 128. In one embodiment, the electrical component delivers a stimulus within a given voltage. In another embodiment, the electrical component is adjustable to deliver a stimulus within a range of voltages. Electrical stimulus perception thresholds can range from 50 μA to 2 mA. The current threshold for pain varies between 1 and 6 mA and the perception threshold seems to be more dependent on the total amount of current rather than the current density. Currents above 2 mA may induce muscle contraction, but up to 25 mA generally does not affect heart and respiratory functions. For cosmetic applications, the current may range from less than 1 mA to about 2 mA. The electrical distraction mechanism 412 may deliver an electrical stimulus to the user by contacting the distraction stimulus 412 to the biological surface. In some embodiments, the electrical stimulus is delivered while the end effector 400 is in proximity with, but not contacting, the biological surface. Electrical stimulus can be applied to the user through a continuous current, a series of pulses, or other method of delivery.

Figure 4J:
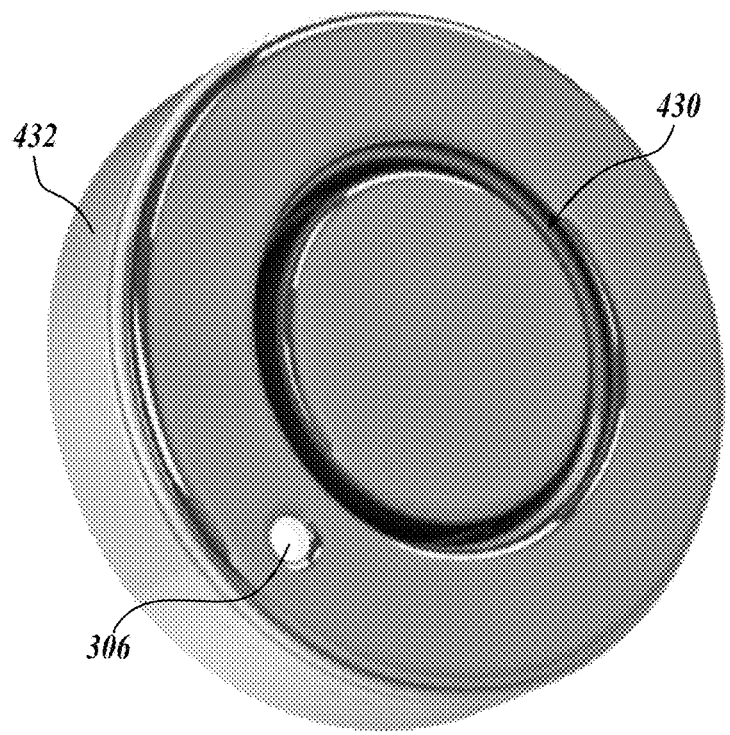

As shown in FIG. 4J, a distraction mechanism 412 in the form of a heating or cooling element can be located on both the inner portion 430 and the outer portion 432. In some embodiments, the inner portion 430, the outer portion 432 or selected positions on either portion may heat up or cool down to provide temperature stimulus during the light therapy.

Figure 5:
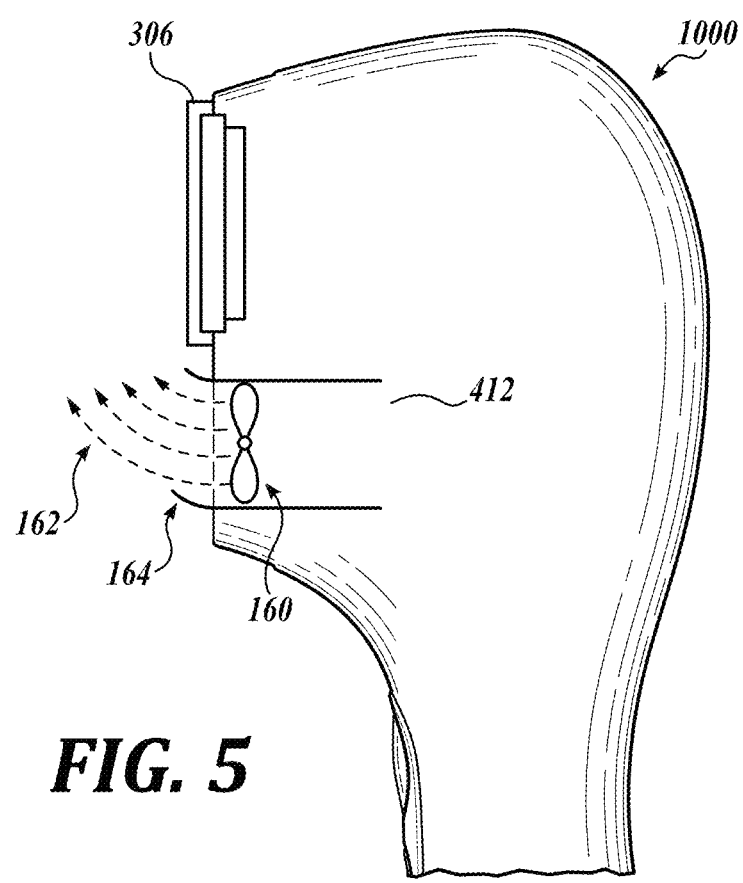
FIG. 5 is a schematic diagram of an example device in accordance with the present technology.

In some embodiments, the distraction mechanism 412 is a mechanical and/or temperature stimulus, provided by an air-cushion head. FIG. 5 is an example embodiment of an air cushion distraction mechanism. The method may include activating an air mover 160 that is located on the body to provide a cushion of flowing air 162 around the end effector 400. The device may include a source of air distraction mechanism 412 that directs an air stream to the region within the area of distraction. The source of air may include an air mover 160, such as a fan or blower, disposed within an air conduit 164 that is shaped to provide the air stream at the surface of the region. In some embodiments, the air may be cooled or warmed to provide temperature distraction. In some embodiments, one or more temperature control elements disposed within the device 1000 adjust the temperature of the air. Non-limiting examples of the temperature control elements include thermoelectric cooling elements including Peltier coolers, electric heating elements including resistive heating coils, etc.

FIGS. 6A-6D are graphs of methods of treatment showing the relationship between a subject's pain threshold, the treatment administered, and the distraction mechanism employed. The horizontal axis shows time. The vertical axis shows intensity of pain in arbitrary units. The dash line labeled "Pain Threshold" is the subject's pain threshold. The dot line labeled "Treatment" is the light therapy the subject is administering. Finally, the solid line labeled "Distraction" is the distraction mechanism implemented as the subject administers treatment.

Figure 6A:
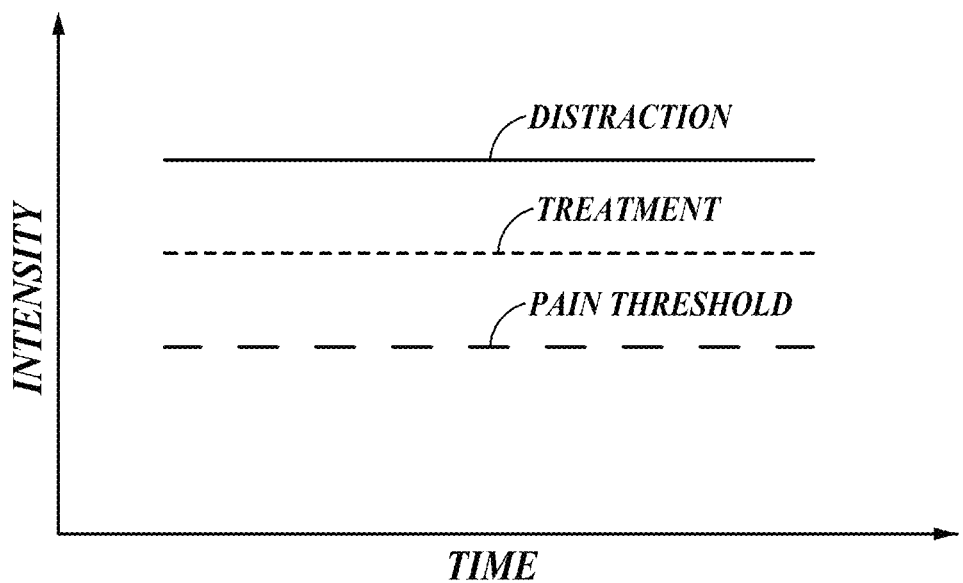
FIGS. 6A-6D are graphs showing the relationship between a subject's pain threshold, the treatment being administered, and the distraction stimulus applied in accordance with the present invention.

FIG. 6A is one example of the method of treatment. While the subject's pain threshold remains constant throughout the treatment, the treatment may be administered at an intensity higher than the subject's pain threshold, because the distraction is administered at a higher intensity than the treatment. As a result of relatively high intensity of the distraction, the subject tends to not notice the pain caused by the treatment. Therefore, the distraction allows the subject to continually apply the treatment with reduced discomfort.

Figure 6B:
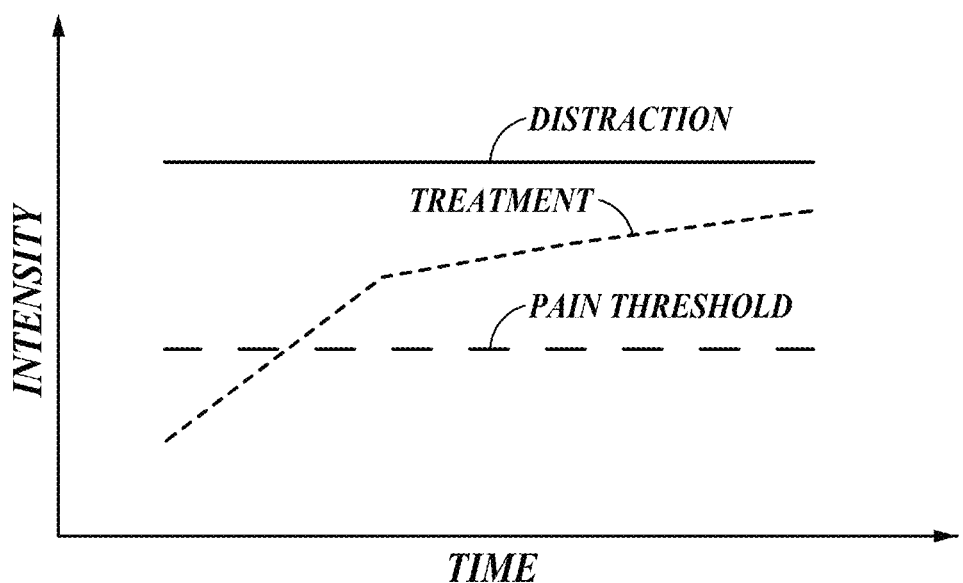

FIG. 6B is another example method of treatment. While the intensity of distraction mechanism remains constant, the subject can increase the amount of light treatment, starting below the pain threshold and eventually increasing the intensity (or power density) of the light treatment above the pain threshold. By implementing a distraction mechanism, the subject can increase the intensity of the treatment over time without major discomfort.

Figure 6C:
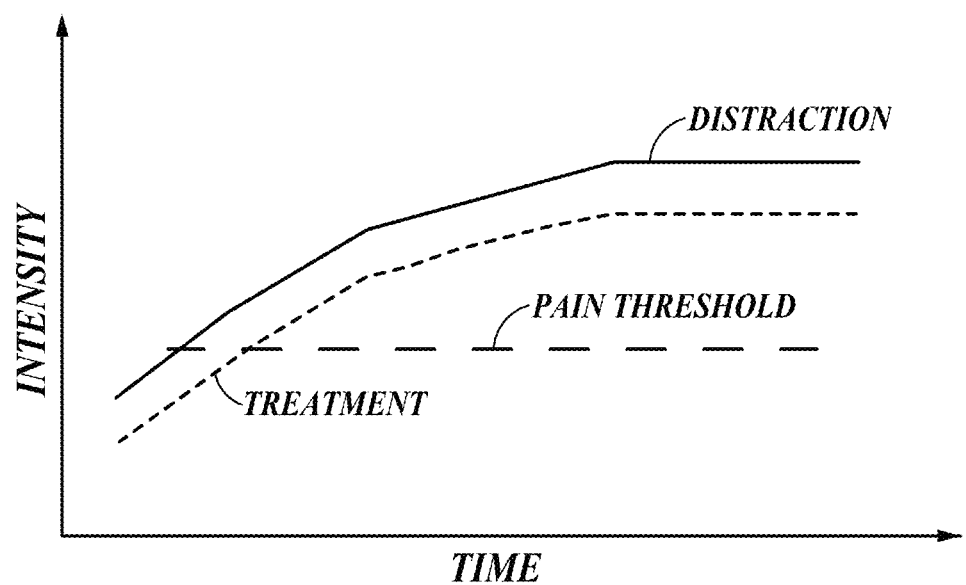

FIG. 6C is another example method of treatment. In this method, the subject increases the intensity of the distraction proportionally with the intensity of the treatment. For example, the subject starts administering light therapy and the distraction at an intensity that is lower than the subject's pain threshold. Next, the subject gradually increases the intensity of the treatment while simultaneously and proportionally increasing the intensity of the distraction mechanism to surpass the subject's pain threshold. Eventually, the treatment may level off as shown in FIG. 6C and settle in a range of higher intensity then it could have in absence of the distraction mechanism. In this way, a subject can administer a higher level of treatment intensity with reduced discomfort.

Figure 6D:
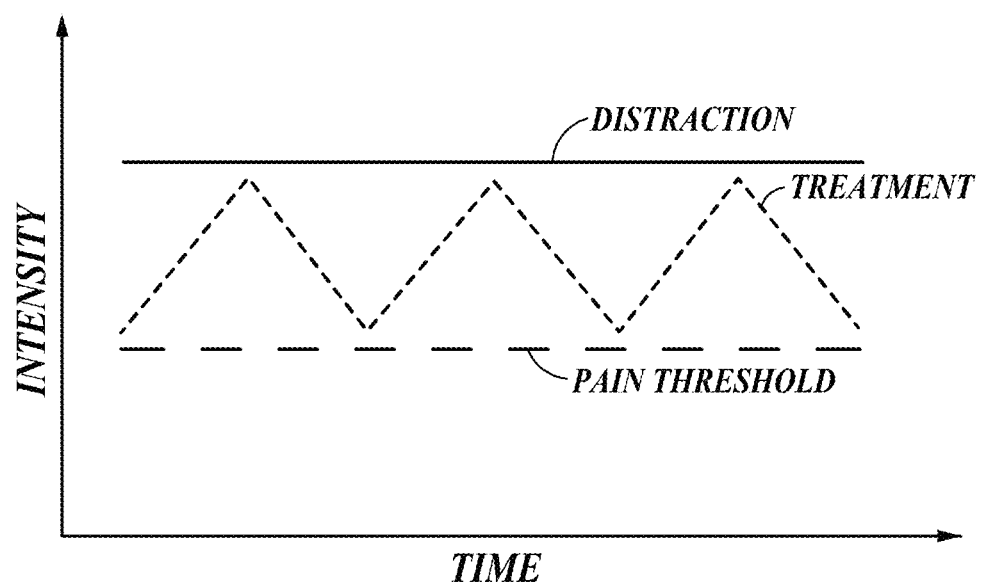

FIG. 6D shows another example method of treatment. In this method, the intensity of the light treatment fluctuates over time. In the illustrated method, the intensity of the treatment fluctuates in a periodic manner, but the treatment may also be administered in a series of bursts, pulses, or other treatment intensities. The distraction applied to the subject stays constant as the treatment is being administered, even when the treatment varies in intensity over time. In this way, the subject can administer variable treatment intensity at a level above their pain threshold while experiencing reduced discomfort.

Figure 7:
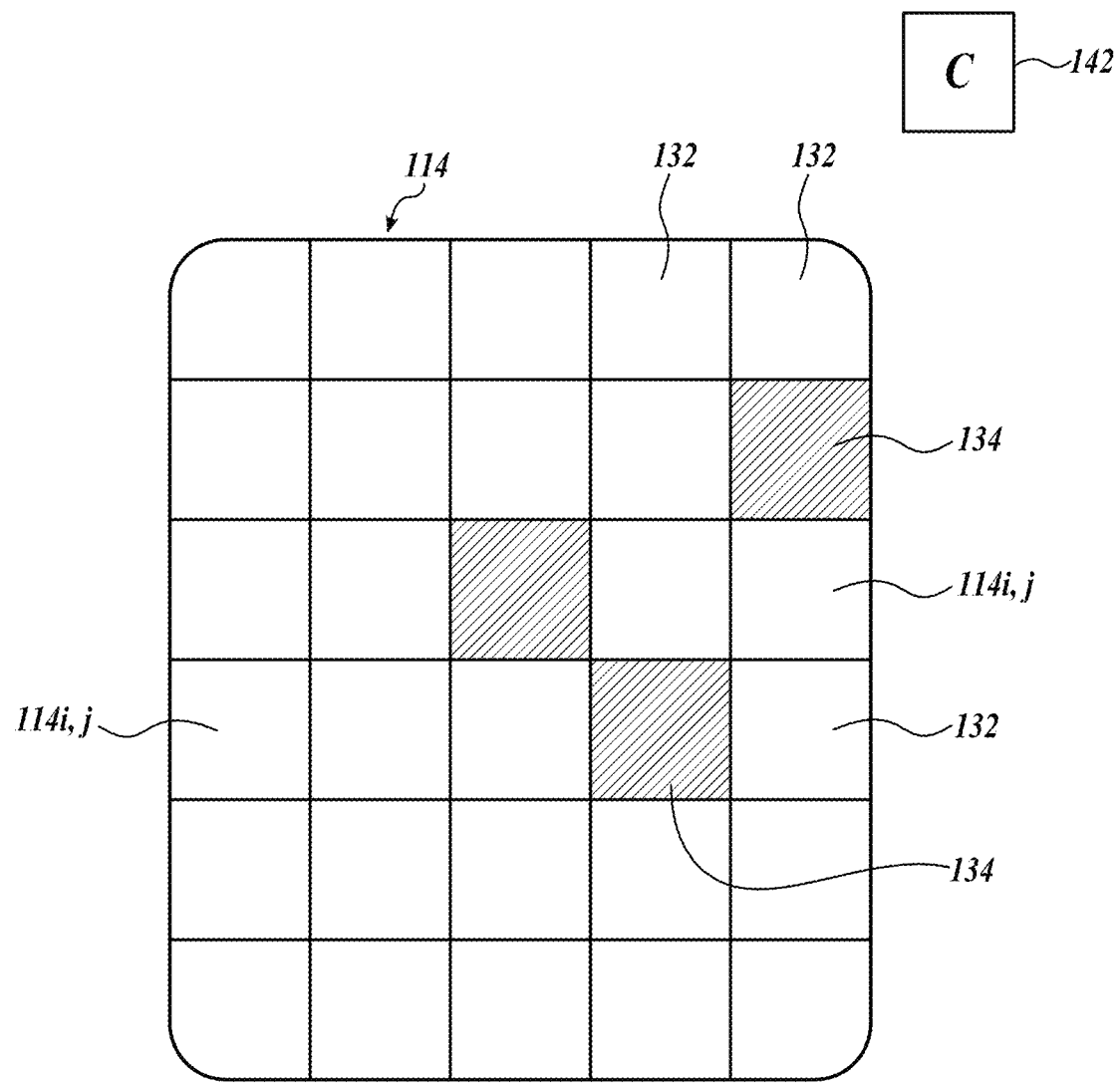
FIG. 7 is a schematic diagram of a light therapy device electrode system in accordance with the present technology.

FIG. 7 is a schematic diagram of a light therapy device electrode system in accordance with the present technology. In some embodiments, a controller 142 responds to an unsafe amount of exposure to light treatment by sending a signal for the source to be moved away from the region on the biological surface toward a second region. The controller 142 may respond to an unsafe power intensity by sending control data to the electronic components of the treatment device 1000 to turn off the treatment. In some embodiments the treatment is generated by a plurality of pixelated electrodes 114$i,j$ arranged in a matrix, as shown in FIG. 7. The pixelated electrodes 114$i,j$ may be individually addressable by the controller 142, where the controller determines a discharge power for a given pixelated electrode 114. Individual pixelated electrodes 114$i,j$ can be controlled to administer light therapy (pixel 132), as well as to turn off the light therapy (pixel 134). In some embodiments, some of the pixelated electrodes 114$i,j$ may be addressable to deliver electric stimulus as distraction.

The components of the treatment device system 1000 may communicate directly through wired and powered connections. These components may communicate to each other via a network (not shown), which may include suitable communication technology including, but not limited to, wired technologies such as DSL, Ethernet, fiber optic, USB, and Firewire; wireless technologies such as WiFi, WiMAX, 3G, 4G, LTE, and Bluetooth; and the Internet.

Figure 8:
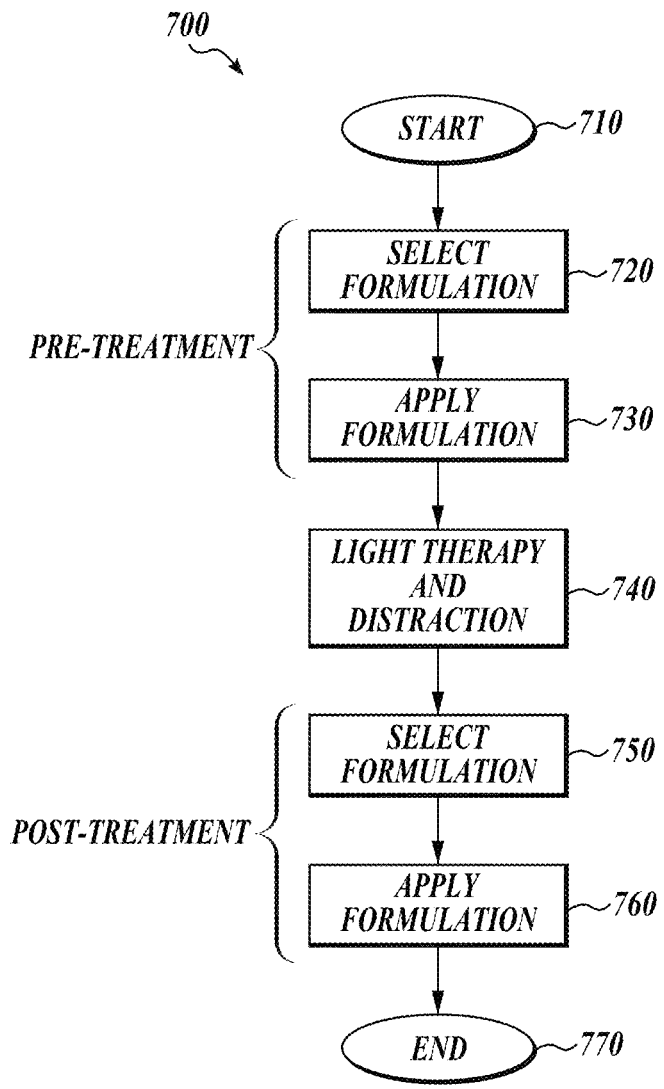
FIG. 8 is a flowchart of a method of light therapy treatment in accordance with the present technology.

In some embodiments, the controller 142 includes a non-transitory computer readable medium having computer executable instructions and data stored thereon that cause, in response to execution by one or more processors of a computing device, the computing device to implement a method of treatment 700 as described herein and illustrated in FIG. 8.

FIG. 8 is a flowchart of a method 700 of light therapy treatment in accordance with the present technology. In some embodiments, the method may include additional steps or may be practiced without all steps illustrated in the flow chart. Method 700 begins at block 710 where the treatment is started. The combination of blocks 720 and 730 is the pre-treatment stage of the method 700. In block 720, a user may select a pre-treatment cosmetic formulation to apply before administering light therapy. In block 730, the subject can then apply the selected formulation to the biological surface (i.e. skin) where the he or she would like to apply treatment.

In block 740, the skincare device 1000 applies the light therapy from one or more light sources 306, and at the same time, applies the distraction stimulus from one or more distraction mechanisms 412. In some embodiments, the treatment and distraction are applied to the area on the biological surface where a subject has applied the pretreatment formulation.

The combination of blocks 750 and 760 is the post-treatment stage of the method 700. In block 750, the user may select a post-treatment cosmetic formulation to apply to the biological surface after administering the light therapy and distraction stimulus. In some embodiments, the post-treatment formulation is the same as the pretreatment cosmetic foundation. In block 760, the user applies the selected formulation to the biological surface where the treatment has been administered. The method 700 ends in block 770.

Many embodiments of the technology described above may take the form of computer- or controller-executable instructions, including routines executed by a programmable computer or controller. Those skilled in the relevant art will appreciate that the technology can be practiced on computer/controller systems other than those shown and described above. The technology can be embodied in a special-purpose computer, controller or data processor that is specifically programmed, configured or constructed to perform one or more of the computer-executable instructions described above. Accordingly, the terms "computer" and "controller" as generally used herein refer to any data processor and can include Internet appliances and hand-held devices (including palm-top computers, wearable computers, cellular or mobile phones, multi-processor systems, processor-based or programmable consumer electronics, network computers, mini computers and the like).

From the foregoing, it will be appreciated that specific embodiments of the technology have been described herein for purposes of illustration, but that various modifications may be made without deviating from the disclosure. For example, in some embodiments the counter or controller may be based on a low-power buck regulator connected to a capacitor. Moreover, while various advantages and features associated with certain embodiments have been described above in the context of those embodiments, other embodiments may also exhibit such advantages and/or features, and not all embodiments need necessarily exhibit such advantages and/or features to fall within the scope of the technology. Accordingly, the disclosure can encompass other embodiments not expressly shown or described herein.

The present application may also reference quantities and numbers. Unless specifically stated, such quantities and numbers are not to be considered restrictive, but exemplary of the possible quantities or numbers associated with the present application. Also, in this regard, the present application may use the term "plurality" to reference a quantity or number. In this regard, the term "plurality" is meant to be any number that is more than one, for example, two, three, four, five, etc. The terms "about," "approximately," etc., mean plus or minus 5% of the stated value.

The principles, representative embodiments, and modes of operation of the present disclosure have been described in the foregoing description. However, aspects of the present disclosure, which are intended to be protected, are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure as claimed.

What is claimed is:

1. A method of administering light treatment to a biological surface comprising:
   administering light therapy from one or more light sources attached to a skincare device, wherein the light therapy is configured to generate a first pain level to a user; and
   administering distraction stimulus from one or more distraction mechanisms attached to the skincare device, wherein the distraction stimulus is configured to distract the user from a discomfort caused by the light therapy by generating a second pain level to the user, wherein each of the first pain level and the second pain level is higher than a pain threshold of the user, and wherein the second pain level is higher than the first pain level.

2. The method of claim 1, wherein the one or more light sources are configured to administer light at multiple wavelengths.

3. The method of claim 1, wherein the one or more distraction mechanisms comprise a mechanical distraction mechanism configured to provide a mechanical stimulus to the biological surface.

4. The method of claim 3, wherein the mechanical stimulus comprises stretching the biological surface.

5. The method of claim 3, wherein the mechanical stimulus comprises brushing the biological surface.

6. The method of claim 1, wherein the one or more distraction mechanisms comprise a thermal distraction mechanism configured to provide a thermal stimulus to the biological surface.

7. The method of claim 1, wherein the one or more distraction mechanisms comprise an electrical distraction mechanism configured to provide an electrical stimulus to the biological surface.

8. The method of claim 1, further comprising contacting the skincare device with the biological surface.

9. The method of claim 1, further comprising placing the skincare device proximal to the biological surface.

10. A skincare device having an end effector comprising:
    a light therapy unit including one or more light sources configured to administer a light therapy by generating a first pain level to a user; and
    a distraction unit operably coupled to the light therapy unit, the distraction unit comprising one or more distraction mechanisms configured to generate a distraction stimulus that distracts a user from a discomfort caused by the light therapy by generating a second pain level to the user, wherein each of the first pain level and the second pain level is higher than a pain threshold of the user, and wherein the second pain level is higher than the first pain level.

11. The skincare device of claim 10, wherein the one or more light sources are a first plurality of light sources configured to administer a light stimulus having a first wavelength, and wherein the distraction unit includes a second plurality of light sources configured to a administer a distraction stimulus at a second wavelength different from the first wavelength.

12. The skincare device of claim 10, wherein the one or more light sources are a first plurality of light sources configured to administer a light stimulus at a first duty cycle, and wherein the distraction unit includes a second plurality of light sources configured to a administer a distraction stimulus at a second duty cycle different from the first duty cycle.

13. The skincare device of claim 10, further comprising a power source coupled to the light therapy unit and the distraction unit by a switch, the distraction unit being configured to administer the distraction stimulus by controlling the switch.

14. The skincare device of claim 10, wherein the end effector is removably attached to a body.

15. The skincare device of claim 10, wherein the one or more light sources comprises a first plurality of light sources configured to administer light within a given wavelength, and a second plurality of light sources configured to administer light therapy within a different given wavelength.

16. The skincare device of claim 10, wherein the end effector comprises an outer portion that at least partially surrounds an inner portion.

17. The skincare device of claim 10, wherein the one or more distraction mechanisms include a mechanical distraction mechanism configured to provide mechanical stimulus to the biological surface.

18. The skincare device of claim 10, wherein the one or more distraction mechanisms include a thermal distraction mechanism configured to provide thermal stimulus to the biological surface.

19. The skincare device of claim 10, wherein the one or more distraction mechanisms include an electrical distraction mechanism configured to provide electrical stimulus to the biological surface.

20. The skincare device of claim 11, wherein the one or more distraction mechanisms are located on the body of the device.

21. The skincare device of claim 11, wherein the one or more light sources are located on the body of the device.

* * * * *

UNITED STATES PATENT AND TRADEMARK OFFICE
CERTIFICATE OF CORRECTION

PATENT NO. : 11,235,167 B2
APPLICATION NO. : 16/863529
DATED : February 1, 2022
INVENTOR(S) : L. Truong It is certified that error appears in the above-identified patent and that said Letters Patent is hereby corrected as shown below:

In the Claims

| Column | Line | |
|---|---|---|
| 12 | 61 | change "to a administer" to -- to administer -- |
| 13 | 1 | change "to a administer" to -- to administer -- |

Signed and Sealed this
Seventh Day of February, 2023

Katherine Kelly Vidal
*Director of the United States Patent and Trademark Office*